(12) United States Patent
Reddy et al.

(10) Patent No.: US 10,892,048 B2
(45) Date of Patent: Jan. 12, 2021

(54) MACHINE LEARNING PILL IDENTIFICATION

(71) Applicants: Puli Pravin Reddy, Atlanta, GA (US); Igor Zamlinsky, Roswell, GA (US)

(72) Inventors: Puli Pravin Reddy, Atlanta, GA (US); Igor Zamlinsky, Roswell, GA (US)

( * ) Notice: Subject to any disclaimer, the term of this patent is extended or adjusted under 35 U.S.C. 154(b) by 12 days.

(21) Appl. No.: 16/144,422

(22) Filed: Sep. 27, 2018

(65) Prior Publication Data

US 2019/0096517 A1    Mar. 28, 2019

Related U.S. Application Data

(60) Provisional application No. 62/564,668, filed on Sep. 28, 2017.

(51) Int. Cl.
| | | |
|---|---|---|
| *G16H 20/13* | (2018.01) | |
| *A61J 1/03* | (2006.01) | |
| *G06K 9/00* | (2006.01) | |
| *G06K 9/20* | (2006.01) | |
| *G06K 9/46* | (2006.01) | |
| *G06K 9/62* | (2006.01) | |
| *G01N 21/25* | (2006.01) | |
| *G16H 50/20* | (2018.01) | |
| *G16H 30/40* | (2018.01) | |
| *G16H 50/70* | (2018.01) | |

(52) U.S. Cl.
CPC ............... *G16H 20/13* (2018.01); *A61J 1/03* (2013.01); *G06K 9/00671* (2013.01); *G06K 9/2027* (2013.01); *G06K 9/4604* (2013.01); *G06K 9/4642* (2013.01); *G06K 9/6204* (2013.01); *G01N 21/25* (2013.01); *G16H 30/40* (2018.01); *G16H 50/20* (2018.01); *G16H 50/70* (2018.01)

(58) Field of Classification Search
CPC ........ G16H 20/13; G16H 50/20; G16H 30/40; G16H 50/70; A61J 1/03; G01N 21/25; G06K 9/4604; G06K 9/6204; G06K 9/4642; G06K 9/2027; G06K 9/00671
See application file for complete search history.

(56) References Cited

U.S. PATENT DOCUMENTS

| | | | | |
|---|---|---|---|---|
| 5,819,953 A | * | 10/1998 | Julius .................... | B07C 5/36 209/561 |
| 7,747,454 B2 | * | 6/2010 | Bartfeld ................ | G16H 70/40 705/3 |
| 2005/0092660 A1 | * | 5/2005 | Vasiadis ............ | B65G 47/1457 209/576 |
| 2013/0188038 A1 | * | 7/2013 | Tanimoto ................ | A61J 3/06 348/86 |

(Continued)

*Primary Examiner* — Brandon J Miller
(74) *Attorney, Agent, or Firm* — Thomas | Horstemeyer, LLP (57) ABSTRACT

Disclosed are various embodiments for automated pill identification using lighting devices and machine learning routines. A computing device may selectively control illumination of a pill provided at an imaging position by a pill dispensing system. The computing device may direct an imaging device to capture image data of the pill during illumination of the pill. Also, the computing device may generate a digital fingerprint of the pill and determine an identity of the pill based at least in part on a comparison of the digital fingerprint to a digital fingerprint library. A machine learning routine may be applied to improve future detection of the identity of the pill.

20 Claims, 5 Drawing Sheets

(56) References Cited

U.S. PATENT DOCUMENTS

| | | | |
|---|---|---|---|
| 2013/0279774 A1* | 10/2013 | Helgason | A61J 7/0084 |
| | | | 382/128 |
| 2017/0219497 A1* | 8/2017 | Shin | G01N 21/8806 |
| 2018/0082410 A1* | 3/2018 | Schulte | G06T 7/75 |
| 2018/0280243 A1* | 10/2018 | Velani | A61J 7/0076 |
| 2020/0027212 A1* | 1/2020 | Foubet | G16H 20/13 |

* cited by examiner

```
<PILL>
    <NAME>Brintellix 5mg</NAME>
    <AREA>10570.000000</AREA>
    <PERIMETER>407.999999</PERIMETER>
    <FULL_AREA>10676.000000</FULL_AREA>
    <CONTOUR>
        <X>369,368,350,349,341,340,334,333,329,328,324...</X>
        <Y>163,164,164,165,165,166,166,167,168,168,169...</Y>
    </COUNTER>
    <HISTOGRAM>
        <R>...</R>
        <G>...</G>
        <B>...</B>
    </HISTOGRAM>
</PILL>
<PILL>
    <NAME>Brintellix 10mg</NAME>
    <AREA>10543.000000</AREA>
    <PERIMETER>407.960449</PERIMETER>
    <FULL_AREA>10640.50000</FULL_AREA>
    <CONTOUR>
        <X>308,307,303,302,299,298,297,296,294,293,292...</X>
        <Y>195,196,196,197,197,198,199,199,200,200,201...</Y>
    </COUNTER>
    <HISTOGRAM>
        <R>...</R>
        <G>...</G>
        <B>...</B>
    </HISTOGRAM>
</PILL>
```

MACHINE LEARNING PILL IDENTIFICATION

CROSS-REFERENCE TO RELATED APPLICATION

This application claims the benefit of and priority to U.S. Provisional Patent Application No. 62/564,668 entitled "MACHINE LEARNING PILL IDENTIFICATION," filed Sep. 28, 2017, the contents of which being incorporated herein by reference in their entirety.

FIELD OF THE INVENTION

The present invention relates to automated, real-time, and accurate pill identification for improving medication adherence and reducing medication errors. Automated and machine-learning based systems may benefit health care organizations in accurate pill sorting, dispensation, and use as will become appreciated. The embodiments described herein may be used with pill sorting machines or other pill dispensing systems, as will be discussed.

BACKGROUND

A majority of prescription medications are dispensed in pill form, as opposed to injectables, transdermal delivery systems, or inhalants. Medication mistakes result from improper identification of pills, which is a significant contributor to medication errors. Notably, medication errors have a reported incidence as high as 40% by some authors. Improper usage reduces pharmacologic efficacy of medications and decreases clinical outcomes. Suboptimal clinical outcomes are an added burden to the health care system as measured by outcomes and cost. Furthermore, incorrect use of medications may result in adverse events requiring additional medical interventions further burdening the healthcare system.

Improper medication usage is a multi-factorial problem. However, it is clear that physical and cognitive barriers contribute to incorrect pill identification by trained healthcare professionals as well as an end-user or patient. The issue of misidentifying pills is encountered both within healthcare institutions by educated and trained healthcare professionals, as well as in household settings by patients.

There are no automated visual pill recognition systems available to an end-user or a patient. Additionally, there are no systems which may be used with a personal digital assistant (PDA), mobile phone, or other client device as a client application, or "app." Visual recognition systems with application in the healthcare sector appear to be employed as home aids or patient monitoring. However, these applications are presently not automated and continue to require trained human input.

BRIEF SUMMARY OF INVENTION

Various embodiments for an automated pill identification system are disclosed. In a first embodiment, the automated pill identification system may include (i) a pill dispensing system comprising at least one chamber configured to move a pill from an original position to an imaging position; (ii) a first lighting device configured to illuminate the pill residing in imaging position from underneath the pill; (iii) an imaging device positioned to capture image data of the pill residing in the imaging position; (iv) a second lighting device configured to illuminate the pill while in the imaging position from above the pill; and (v) at least one computing device. The at least one computing device may be configured to selectively control at least one of the first lighting device to illuminate the pill from underneath; direct the imaging device to capture image data of the pill during illumination of the pill by the first lighting device; selectively control at least one of the second lighting device to illuminate the pill from above; direct the imaging device to capture the image data of the pill during illumination of the pill by the second lighting device; generate a digital fingerprint of the pill, wherein the digital fingerprint comprises a red-green-blue histogram and a pill edge morphology generated based at least in part on the image data captured by the imaging device; determine an identity of the pill based at least in part on a comparison of the digital fingerprint to a digital fingerprint library; and apply a machine learning routine to improve future detection of the identity of the pill.

In some embodiments, the first light emitting device may include a substantially flat light emitting diode (LED) backlight and the second lighting device comprises a plurality of light emitting diodes (LEDs). The at least one computing device may be further configured to generate a data object for the pill, where the data object comprises a plurality of variables and a plurality of values corresponding to the variables, wherein at least one of the plurality of variables comprises: a pill name, a pill area, a pill perimeter, a pill full area, a pill contour, and pill histogram data. The pill histogram data may include data corresponding to at least one red value, at least one green value, and at least one blue value.

In a second embodiment, the automated pill identification system may include at least one computing device and program instructions stored in memory and executable by the at least one computing device that, when executed, direct the at least one computing device to: (i) selectively control illumination of a pill provided at an imaging position by a pill dispensing system; (ii) direct an imaging device to capture image data of the pill during illumination of the pill; (iii) generate a digital fingerprint of the pill; and determine an identity of the pill based at least in part on a comparison of the digital fingerprint to a digital fingerprint library.

The digital fingerprint may include a red-green-blue histogram generated based at least in part on the image data captured by the imaging device and/or a pill edge morphology generated based at least in part on the image data captured by the imaging device. The pill dispensing system may include at least one chamber. The system may further include (i) a first lighting device configured to illuminate the pill from a position underneath the pill; (ii) an imaging device positioned to capture image data of the pill residing in the at least one chamber of the pill dispensing system; and (iii) a second lighting device configured to illuminate the pill from a position above the pill.

In some embodiments, the image data may include at least a first image and a second image, where the first image is acquired by the imaging device when the pill is illuminated by the first lighting device from a position underneath the pill and the second image is acquired by the imaging device when the pill is illuminated by the second lighting device from a position above the pill. As such, the pill edge morphology may be generated based at least in part on the first image; and the red-green-blue histogram may be generated based at least in part on the second image.

In some embodiments, the second imaging device may include a plurality of light emitting diodes (LEDs); and the at least one computing device may be directed to adjust at least one of: a red value, a blue value, and a green value associated with an illumination of at least one of the plurality of LEDs. The at least one computing device may be further directed to apply a machine learning routine to improve future detection of the identity of the pill.

In another embodiment, a computer-implemented method is disclosed, where the method comprises (i) selectively controlling, by at least one computing device, illumination of a pill provided at an imaging position by a pill dispensing system; (ii) directing, by the at least one computing device, an imaging device to capture image data of the pill during illumination of the pill; (iii) generating, by the at least one computing device, a digital fingerprint of the pill; (iv) determining, by the at least one computing device, an identity of the pill based at least in part on a comparison of the digital fingerprint to a digital fingerprint library; and (v) applying, by the at least one computing device, a machine learning routine to improve future detection of the identity of the pill.

The digital fingerprint may include a red-green-blue histogram generated based at least in part on the image data captured by the imaging device and/or a pill edge morphology generated based at least in part on the image data captured by the imaging device. The method may further include directing, by the at least one computing device, a first lighting device to illuminate the pill from a position underneath the pill and directing, by the at least one computing device, a second lighting device positioned near an imaging device to illuminate the pill from a position above the pill. The image data may include at least a first image and a second image, where the first image is acquired by the imaging device when the pill is illuminated by the first lighting device from the position underneath the pill and the second image is acquired by the imaging device when the pill is illuminated by the second lighting device from the position above the pill. The pill edge morphology may be generated based at least in part on the first image and the red-green-blue histogram may be generated based at least in part on the second image.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the disclosure. Moreover, in the drawings, like reference numerals designate corresponding parts throughout the several views.

DETAILED DESCRIPTION

The present disclosure relates to automated pill identification using lighting devices and machine learning routines. As noted above, improper medication usage is a multifactorial problem as it is clear that physical and cognitive barriers contribute to incorrect pill identification by trained healthcare professionals along with end-users and patients. Misidentifying pills is encountered both within healthcare institutions by educated and trained healthcare professionals, as well as in household settings by patients. Accordingly, various embodiments are describes that correctly identify or verify pills with a high-accuracy, which may improve medication adherence while reducing medication errors.

According to various embodiments describes herein, a system, apparatus, or method may include an automated pill identification system or use thereof that may be employed as a component of a pill dispensation, conveyor, vacuum, or sorting system. In the various embodiments describes herein, pills may be visually identified based on size, shape, color, surface texture, and imprinted or embossed characters.

As commercially available pills are manufactured according to good manufacturing practices (GMP), a consistency in size, shape, texture, color, and identification badges of pills is commonly achieved. In the various embodiments described herein, the physical attributes of a pill, such as a pill size, a pill shape, a pill texture, a pill color, and a pill identification badge, may be used as a basis for consistent and automated visual identification.

In various embodiments described herein, image data may be acquired from reflecting light on or near pills in order to generate red-green-blue (RGB) histograms and/or a pill edge morphology. The image data generated may be generated by one or more imaging devices, such as one or more cameras, as may be appreciated. The image data may be analyzed by one or more computing device, for instance, to generate a red-green-blue histogram and/or a pill edge morphology (also referred to as a "silhouette morphology"). A digital fingerprint of a pill may then be generated based at least in part on the red-green-blue histogram and/or the pill edge morphology, which may be compared to a library of known pills, to identify an identity of the pill. The identity may include a type, dosage, manufacturer, or other information associated with a pill.

In various embodiments described herein, a digital characterization of colors may be employed using the Young-Helmholtz and Maxwell theories of trichromatic color vision. For instance, the primary colors of red, blue, and green may be additively mixed in order to create colors within a color triangle. Colors in a red-green-blue model may be quantified as numerical representations based on the amounts of the primary colors present. The resulting color may be expressed as a red-green-blue triplet as well as illustrated as a red-green-blue histogram.

Pill identification may also be implemented by capturing a pill edge morphology of a pill. For instance, a sharp edge suitable for visual analysis may be generated by "backlighting" the pill in order to generate a silhouette of the edge with minimal refraction. In other words, a lighting device may illuminate the pill from a position beneath or below the pill. As a pill may be presented for visual inspection in a variety of perspectives, identification of the pill edge morphology may be used in combination with a red-green-blue histograms to achieve a high fidelity of pill identification. The visual recognition of pills based on a red-green-blue histograms and the pill edge morphology may be implemented in an automated pill recognition system that may be coupled to or otherwise employed with a medication dispensation, conveyor, vacuum, or sorting system.

There are no automated visual pill recognition systems available to an end-users or patients. Additionally, there are no systems which may be used with a personal digital assistant (PDA), mobile phone, or other client device as a client application, or "app." Visual recognition systems with application in the healthcare sector appear to be employed as home aids or patient monitoring. However, these applications are presently not automated and continue to require trained human input.

With regards to medication adherence by end-users (e.g., patients at home), mechanical devices exist that are designed to organize pills, or medications, by day. These commercially available devices, referred to as "pill boxes," are nothing more than reminders and are highly susceptible to error by an end-user. While pill boxes are certainly useful, they require an educated and carefully organized user. Moreover, pill boxes have not been shown to reduce medication error. Furthermore, attachments exist that may be connected to existing pill bottles, serving as reminders and measuring devices of pill usage. However, a source of error with these attachments is correct pill identification and no devices assisting with proper pill identification, whether during organization of pills or at the point of medication administration.

The invention described herein automatically and efficiently identifies pills with a high degree of accuracy and may be combined with pill sorting and dispensing machines, as well as other systems described herein.

Figure 1:
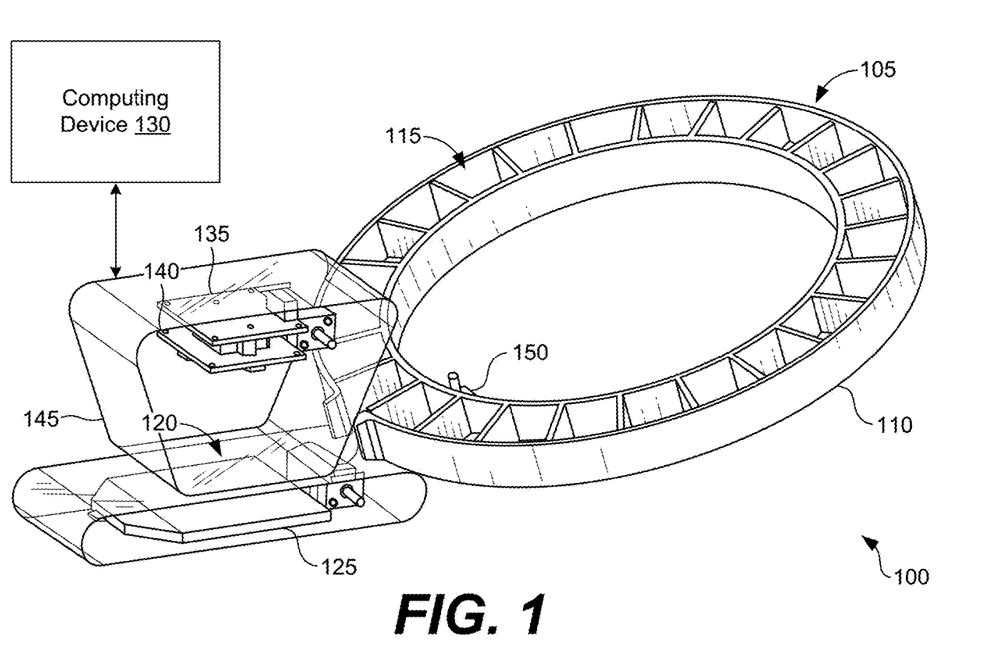
FIG. 1 shows a carousel assembly by which an object pill presented for analysis in a repetitive manner for a combination of data acquisition using lights and silhouette morphology in accordance with various embodiments of the present disclosure.

Turning now to FIG. 1, an example of an automated pill identification system 100 is shown which may include or otherwise be used with a pill dispensing system 105. Notably, the pill dispensing system 105 may include a carousel 110 having one or more chambers 115 although, in alternative embodiments, the pill dispensing system 105 may include a conveyor or other pill moving apparatus. In either case, the pill dispensing system 105 may move a pill from one position to another. In various embodiments described herein, the pill may be moved to an imaging position 120 where image data of the pill may be acquired, as will be discussed. While the imaging position 120 is shown separate from the carousel 110 of the pill dispensing system 105, in some embodiments, image data of a pill may be acquired while the pill is in the carousel 110 or other transport device, as may be appreciated. The carousel 110 may have a twenty-five pill capacity in some embodiments (e.g., twenty-five chambers), or other suitable capacity.

In some embodiments, the imaging position 120 may include a flat surface. Further, in some embodiments, the imaging position 120 may include a transparent or partially transparent surface which permits illumination of the pill using a light source disposed beneath the imaging position 120. To this end, in some embodiments, the automated pill identification system 100 may include a first lighting device 125 configured to illuminate a pill from a position underneath the pill.

The automated pill identification system 100 may further include a computing device 130, an imaging device 135 in data communication with the computing device 130, a second lighting device 140, as well as other components as may be appreciated. Further, in some embodiments, the first lighting device 125 and the second lighting device 145 may be in data communication with the computing device 130 for selectively controlling light, as will be described.

The input device 135 may include an input system of a digital camera (e.g., CCD camera or CMOS camera) or other color image capturing systems. The imaging device 135, which may include a camera in some embodiments, may be enclosed in a housing 145 facing downward, e.g., towards the imaging position 120. Notably, the bottom surface of the housing 145 may include the imaging position 130.

As such, the housing 145 may be transparent or partially transparent, as noted above. The imaging device 135 may be positioned to capture image data of a pill at the imaging position 120 or other position of the pill dispensing system 105. In some embodiments, the imaging device 135 includes the second lighting device 140 positioned thereon for illuminating the imaging position 140 from a position above the pill.

Figure 2:
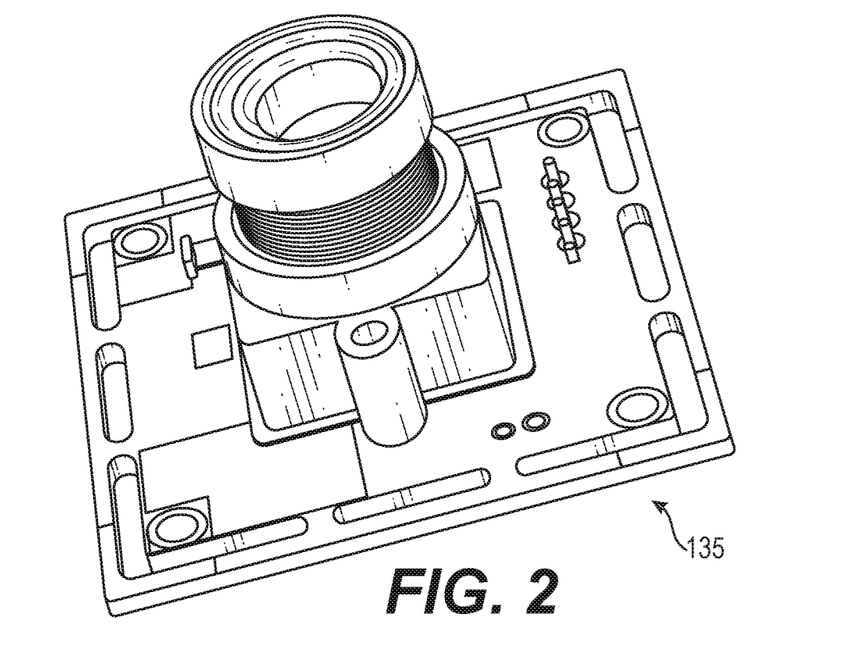
FIG. 2 shows an example of an imaging device comprising a camera in accordance with various embodiments of the present disclosure.

For instance, as shown in FIG. 2, the imaging device 135 may include a universal serial bus (USB) camera. In some embodiments, the imaging device 35 may include a five-million-pixel (5 MP) USB camera or similar device. Further, the imaging device may include a plurality of light emitting diodes (LEDs) (not shown) (i.e., the second lighting device 140) positioned thereon or coupled thereto. In some embodiments, the LEDs may be tunable or selectable controllable by the computing device 130.

Figure 3:
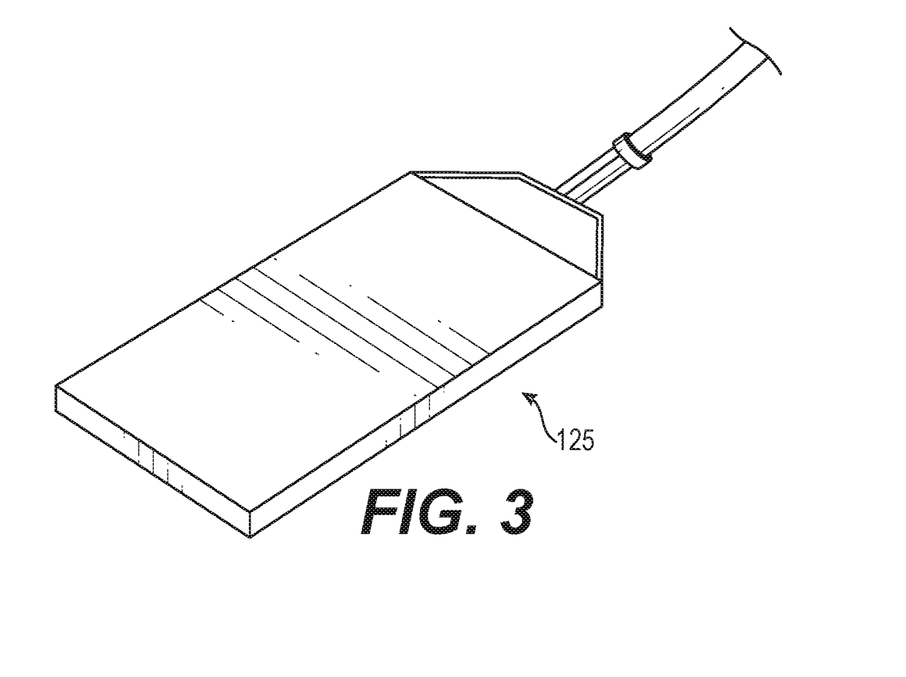
FIG. 3 shows an example of a lighting device or a light array in accordance with various embodiments of the present disclosure.

FIG. 3 illustrates an example of the first lighting device 120, which may include a rectangular and substantially flat panel lighting device, such as an LED device. Referring back to FIG. 1, the first lighting device 120 may be positioned below the bottom surface of the housing 145.

Referring back to FIG. 1, the computing device 130 may include one or more computing devices 130 in some embodiments as may be appreciated. The computing device 130 may include at least one processor circuit, for example, having a processor and a memory, both of which being coupled to a local interface. To this end, the computing device 130 may comprise, for example, at least one server computer or like device. The local interface may comprise, for example, a data bus with an accompanying address or control bus, or other bus structure, as can be appreciated.

The computing device 130 may include one or more program instructions stored in memory thereon, where the program instructions may include an application, service, or similar software. Through installation or execution of the program instructions, the computing device 130 may be configured to selectively control, configure, or operate the first lighting device 125, the imaging device 135, the second lighting device 140, as well as other controllable hardware of the automated pill identification system 100. Further, the computing device 130 may implement (or communicate with a service over a network that implements) one or more machine learning (ML) routines to improve the identification or classification of pills being images, as well be described.

The computing device 130 may, for example, direct at least one of the first lighting device 125 and the second lighting device 140 to illuminate a pill at the imaging position 120 or other position. Further, the computing device 130 may direct the imaging device to capture image data (e.g., generating one or more digital image files) of the pill during illumination of the pill or when the pill is not being illuminated.

In some embodiments, the computing device 130, or a device connected thereto, may generate a digital fingerprint of the pill. The digital fingerprint of the pill comprises a red-green-blue histogram and/or a pill edge morphology generated based at least in part on the image data captured by the imaging device 135. To this end, the computing device 140 may determine an identity of the pill based at least in part on a comparison of the digital fingerprint to a digital fingerprint library stored in memory. Further, the machine learning routines may be applied during identification or verification of an identification of the pill to improve future detection of the identity of the pill, as may be appreciated.

As may be appreciated, the pill dispensing system 105 may present pills for analysis in a repetitive manner. For instance, the carousel 110 may rotate using one or more motors 150. The carousel 110 may be positioned at an incline relative to the imaging station 120, which may be substantially flat and non-angled, causing the pill to slide from a chamber 115 of the carousel 110 onto the imaging station 120 or similar surface. As such, a variety of pills may be presented for analysis in a repetitive manner for data acquisition using the first lighting device 125 and/or the second lighting device 140, and a pill edge morphology. The resulting image data may be used to assemble a comprehensive database for machine learning.

Next, an example operation of the automated pill identification system 100 is described. An object, such as a pill, may be illuminated with the first imaging device 125 and/or the second imaging device 140, which each may include one or more light emitting diodes. In some embodiments, the light emitting diodes may be configured to emit light in accordance with the following frequencies: blue (≅6.67× 1014 Hz); green (≅5.2 1014 Hz); and red (≅4.8×1014 Hz).

The pill may be positioned on the imaging position 125, which may include a surface of the first imaging device 125 or a surface having the first imaging device 125 positioned underneath. The first imaging device 125 may be switched on or off by the computing device 130, for instance, to generate either a black or white background which may be used to generate a silhouette of a body or a morphology of the pill that clearly denotes a pill shape.

In some embodiments, the imaging device 140, which may include a color camera assembly may be configured for image data acquisition, or image capture, by exposing the pill to red, blue, and/or green light frequencies emitted by the second lighting device 140, or other light sources. In some embodiments, the second lighting device 140 or other light source may be secured to an external housing of a camera lens at a fixed or variable distance, as may be appreciated. An example of image data acquired during this process is shown in image 409 of FIG. 4 and image 509 of FIG. 5.

Further, the computing device 130 may generate separate sets of data based at least in part on the shape of the pill and edge morphology of the pill. The representation of either a segment or the whole of the pill silhouette may be captured for analysis.

Figure 4:
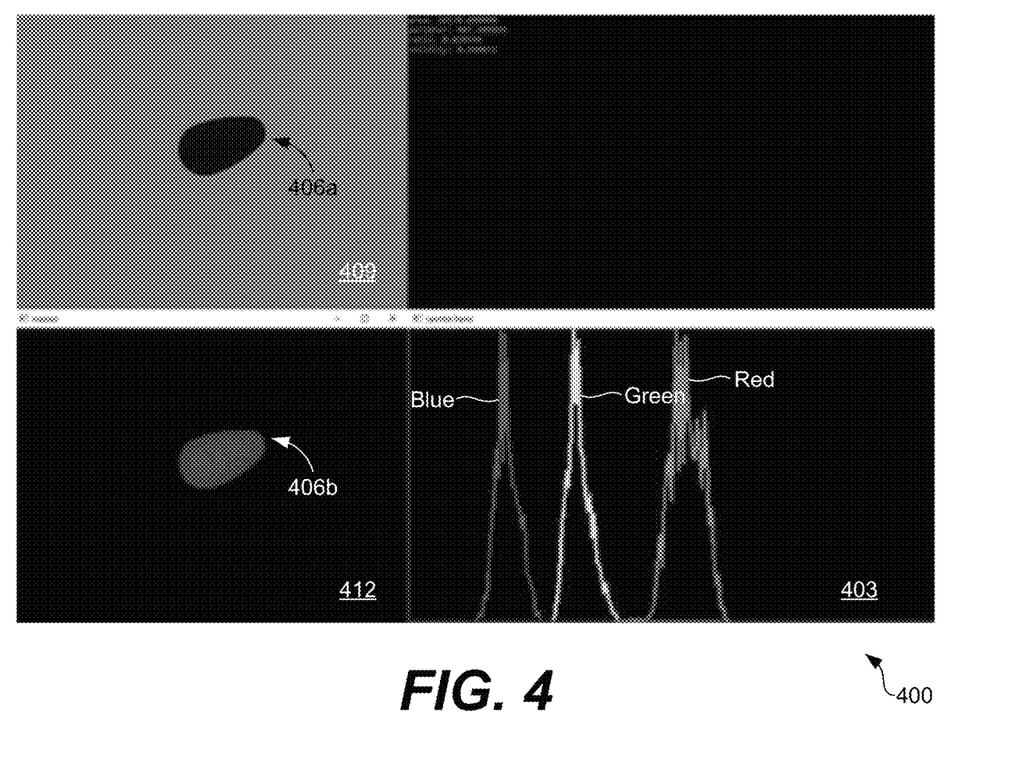
FIG. 4 shows a red-green-blue (RGB) histogram representing a unique manufactured proprietary pill generated in accordance with various embodiments of the present disclosure.
Figure 5:
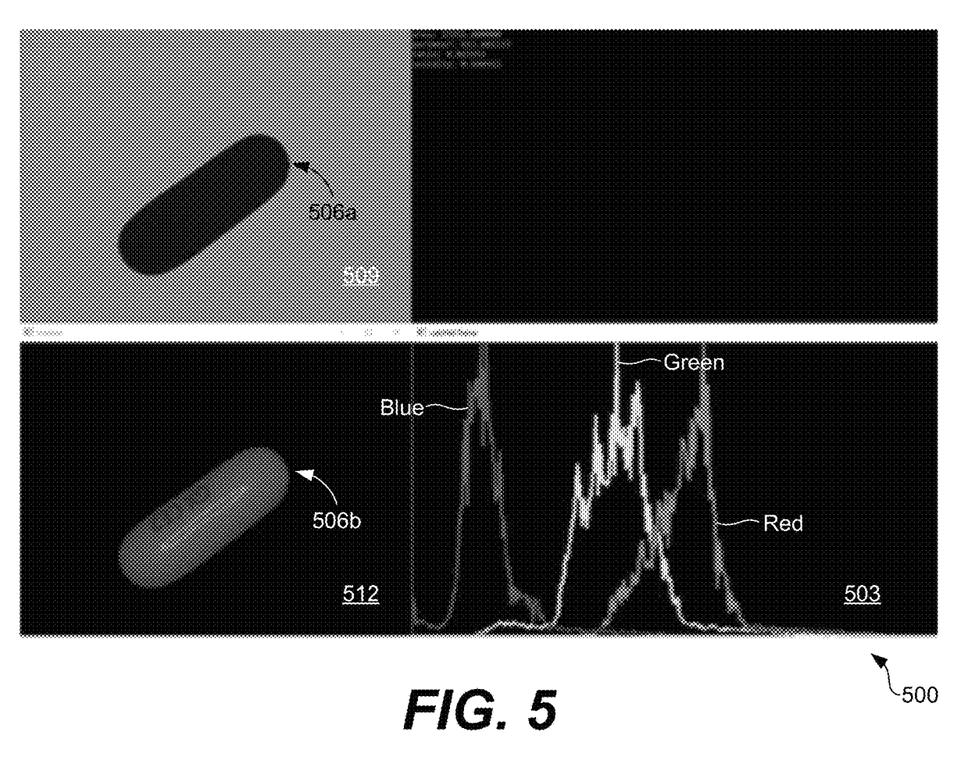
FIG. 5 shows an RGB histogram representing a second proprietary pill in accordance with various embodiments of the present disclosure.

The first imaging device 125 may be selectively turned off, such that the pill appears to rest on a uniform dark surface or otherwise having a light absorbing background. Then, the second imaging device 125 may be turned on to illuminate the pill and capture image data while the pill is illuminated. An example of this image data is shown in image 412 of FIG. 4 and image 512 of FIG. 5. The image data acquired in this step may be used to create a multichannel color red-green-blue histogram, as shown in FIG. 4 and FIG. 5. Notably, each pill will generates a unique red-green-blue histogram based on color variation, tonal intensity, and/or other physical characteristics.

The relationship between the red-green-blue space to a hue-saturation-intensity (HIS) space may be governed by the following mathematical formulae:

$$I = \frac{(R+G+B)}{3}, \qquad \text{(eq. 1)}$$

$$S = 1 - 3/(R+G+B) - (R, G, B), \qquad \text{(eq. 2)}$$

$$H = \cos^{-1}\left[1/2\ (R-G) + \frac{R-B}{(R-G)2} + (R-B)(G-B)\right]^{1/2}. \qquad \text{(eq. 3)}$$

Thus, color and tonal gradients may be mathematically measured and quantified. The red-green-blue histogram may be combined with a silhouette morphology in order to generate a digital signature or a digital fingerprint of a pill that accurately and consistently represents the pill. The raw data acquired from the reflected light from the pill may be processed using a commercially available microprocessor in some examples.

The computing device 103 may compiling raw image data, or visual data, organize raw data into red-green-blue histograms, generate a monochromatic silhouette morphology, compare processed data with a database of red-green-blue histograms and silhouette morphologies for known pills, and ultimately generate a proper identification of the pill. A reference library may include digital signatures or fingerprints of distinct pills defined by red-green-blue histograms and silhouette morphologies.

Further, one or more machine learning routines may be implemented. For instance, image data, or the red-green-blue histograms or silhouette morphologies dervived therefrom, may be presented for further computational analysis using a machine learning protocol, such as TensorFlow, or other artificial intelligence (AI) platform. As such, continuous real-time improvements in pill recognition may occur. Improved pill recognition by machine learning may be based on a heterogeneity of pill presentations. Permutational computations with a variety of partial pill silhouettes combined with red-green-blue histograms may further add to and refine the database of pill fingerprints. The multiple layers of data classification improves the accuracy with which pills are identified. Artificial intelligence-enabled automated pill recognition systems not only improves pill recognition but makes it possible to identify novel pills for addition to the reference library.

FIG. 4 includes a schematic diagram 400 that includes a red-green-blue histogram 403 of a pill 406a, 406b. Also, a first image 409 of the pill 406a is shown as well as a second image 412 of the pill 406b. Notably, the first image 409 is generated to show a silhouette of the pill 406 while the second image 412 shows color, textures, marking (e.g., identifying information), and/or other physical characteristics on a neutral background.

FIG. 5 includes another schematic diagram 500 that includes a red-green-blue histogram 503 of a pill 506a, 506b different than the pill 406 of FIG. 4. Similar to FIG. 4, a first image 509 of the pill 506a is shown as well as a second image 512 of the pill 506b. The first image 509 may be generated by the computing device 130 to show a silhouette of the pill 506 while the second image 512 may be generated to show color, textures, marking (e.g., identifying information), and/or other physical characteristics of the pill 506b on a neutral background for analysis. Notably, a comparison of the red-green-blue histogram 403 of FIG. 4 with the red-green-blue histogram 503 of FIG. 5 shows a clear distinction between the pills 406, 506. As such, the digital fingerprint of a pill may uniquely identify the pill.

Figure 6:
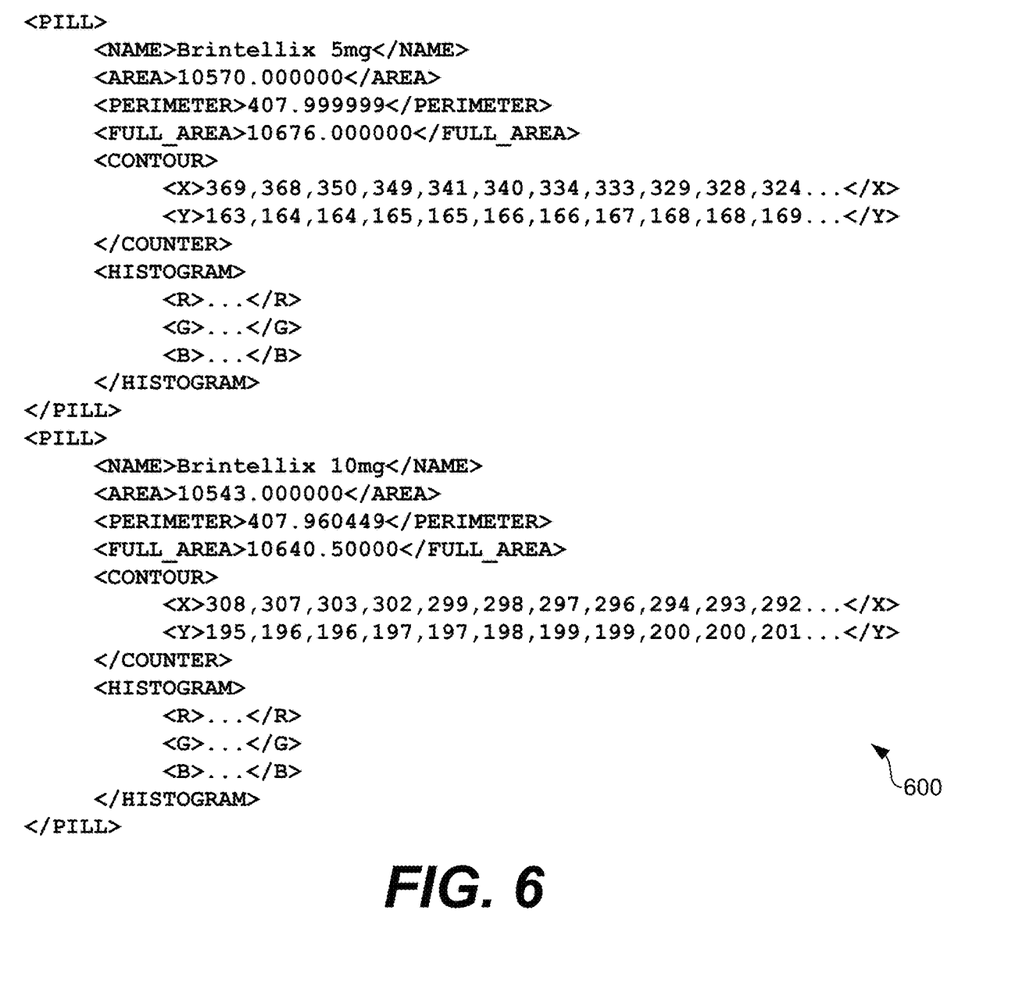
FIG. 6 is an example data object representing a digital signature of an object pill in accordance with various embodiments of the present disclosure.

FIG. 6 includes an example of a data object 600 that may be generated by the computing device 103 for a pill. In some embodiments, the data object 600 may be described as the digital fingerprint of a pill. The data object 600 may include variables and a as well as values corresponding to the variables. Some of the variables may include, for example, a pill name, a pill area, a pill perimeter, a pill full area, a pill contour, and pill histogram data, as well as other information.

Stored in the memory are both data and several components that are executable by the processor. In addition, an operating system may be stored in the memory and executable by the processor. It is understood that there may be other applications that are stored in the memory and are executable by the processor as can be appreciated. Where any component discussed herein is implemented in the form of software, any one of a number of programming languages may be employed such as, for example, C, C++, C#, Objective C, Java®, JavaScript®, Perl, PHP, Visual Basic®, Python®, Ruby, Flash®, or other programming languages.

A number of software components are stored in the memory and are executable by the processor. In this respect, the term "executable" means a program file that is in a form that can ultimately be run by the processor. Examples of executable programs may be, for example, a compiled program that can be translated into machine code in a format that can be loaded into a random access portion of the memory and run by the processor, source code that may be expressed in proper format such as object code that is capable of being loaded into a random access portion of the memory and executed by the processor, or source code that may be interpreted by another executable program to generate instructions in a random access portion of the memory to be executed by the processor, etc. An executable program may be stored in any portion or component of the memory including, for example, random access memory (RAM), read-only memory (ROM), hard drive, solid-state drive, USB flash drive, memory card, optical disc such as compact disc (CD) or digital versatile disc (DVD), floppy disk, magnetic tape, or other memory components.

The memory is defined herein as including both volatile and nonvolatile memory and data storage components. Volatile components are those that do not retain data values upon loss of power. Nonvolatile components are those that retain data upon a loss of power. Thus, the memory may comprise, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM may comprise, for example, static random access memory (SRAM), dynamic random access memory (DRAM), or magnetic random access memory (MRAM) and other such devices. The ROM may comprise, for example, a programmable read-only memory (PROM), an erasable programmable read-only memory (EPROM), an electrically erasable programmable read-only memory (EEPROM), or other like memory device.

Also, the processor may represent multiple processors and/or multiple processor cores and the memory may represent multiple memories that operate in parallel processing circuits, respectively. In such a case, the local interface may be an appropriate network that facilitates communication between any two of the multiple processors, between any processor and any of the memories, or between any two of the memories, etc. The local interface may comprise additional systems designed to coordinate this communication, including, for example, performing load balancing. The processor may be of electrical or of some other available construction.

Although the various systems described herein may be embodied in software or code executed by general purpose hardware as discussed above, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits (ASICs) having appropriate logic gates, field-programmable gate arrays (FPGAs), or other components, etc.

The program instructions described herein may be embodied in the form of source code that comprises human-readable statements written in a programming language or machine code that comprises numerical instructions recognizable by a suitable execution system such as a processor in a computer system or other system. The machine code may be converted from the source code, etc. If embodied in hardware, each block may represent a circuit or a number of interconnected circuits to implement the specified logical function(s).

Also, any logic or application described herein that comprises software or code can be embodied in any non-transitory computer-readable medium for use by or in connection with an instruction execution system such as, for example, a processor in a computer system or other system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system.

The computer-readable medium can comprise any one of many physical media such as, for example, magnetic, optical, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

Further, any logic or application described herein may be implemented and structured in a variety of ways. For example, one or more applications described may be implemented as modules or components of a single application. Further, one or more applications described herein may be executed in shared or separate computing devices or a combination thereof. For example, a plurality of the applications described herein may execute in the same computing device 130, or in multiple computing devices in the same computing environment. Additionally, it is understood that terms such as "application," "service," "system," "engine," "module," and so on may be interchangeable and are not intended to be limiting.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

Therefore, the following is claimed:

1. A system, comprising:
a pill dispensing system comprising at least one chamber configured to move a pill from an original position to an imaging position;
a first lighting device configured to illuminate the pill residing in imaging position from underneath the pill;
an imaging device positioned to capture image data of the pill residing in the imaging position;
a second lighting device configured to illuminate the pill while in the imaging position from above the pill;
at least one computing device being configured to:
selectively control at least one of the first lighting device to illuminate the pill from underneath;
direct the imaging device to capture first image data of the pill during illumination of the pill by the first lighting device;
selectively control at least one of the second lighting device to illuminate the pill from above;
direct the imaging device to capture second image data of the pill during illumination of the pill by the second lighting device;
generate a digital fingerprint of the pill, wherein the digital fingerprint comprises a red-green-blue histogram and a pill edge morphology generated based at least in part on the first image data and the second image data;
determine an identity of the pill based at least in part on a comparison of the digital fingerprint to a digital fingerprint library; and
apply a machine learning routine to improve future detection of the identity of the pill.

2. The system of claim 1, wherein the first light emitting device comprises a substantially flat light emitting diode (LED) backlight; and
wherein the second lighting device comprises a plurality of light emitting diodes (LEDs).

3. The system of claim 1, wherein the at least one computing device is further configured to generate a data object for the pill, wherein the data object comprises a plurality of variables and a plurality of values corresponding to the variables, wherein at least one of the plurality of variables comprises: a pill name, a pill area, a pill perimeter, a pill full area, a pill contour, and pill histogram data.

4. The system of claim 3, wherein the pill histogram data comprises data corresponding to at least one red value, at least one green value, and at least one blue value.

5. A system, comprising:
at least one computing device;
program instructions stored in memory and executable by the at least one computing device that, when executed, direct the at least one computing device to:
selectively control illumination of a pill provided at an imaging position by a pill dispensing system;
direct an imaging device to capture image data of the pill during illumination of the pill from a position above the pill and illumination of the pill from a position beneath the pill;
generate a digital fingerprint of the pill comprising a histogram, the histogram generated based at least in part on the image data captured by the imaging device; and
determine an identity of the pill based at least in part on a comparison of the digital fingerprint to a digital fingerprint library.

6. The system of claim 5, wherein the histogram is a red-green-blue histogram generated based at least in part on the image data captured by the imaging device.

7. The system of claim 6, wherein the digital fingerprint further comprises a pill edge morphology generated based at least in part on the image data captured by the imaging device.

8. The system of claim 7, further comprising the pill dispensing system, the pill dispensing system comprising at least one chamber, the imaging position comprising a position within the at least one chamber.

9. The system of claim 8, further comprising a first lighting device configured to illuminate the pill residing in the at least one chamber from a position underneath the pill.

10. The system of claim 9, further comprising an imaging device positioned to capture image data of the pill residing in the at least one chamber of the pill dispensing system, wherein the imaging device comprises a second lighting device positioned thereon for illuminating the at least one chamber from a position above the pill.

11. The system of claim 10, wherein:
the image data comprises at least a first image and a second image;
the first image is acquired by the imaging device when the pill is illuminated by the first lighting device from a position underneath the pill; and
the second image is acquired by the imaging device when the pill is illuminated by the second lighting device from a position above the pill.

12. The system of claim 11, wherein:
the pill edge morphology is generated based at least in part on the first image; and
the red-green-blue histogram is generated based at least in part on the second image.

13. The system of claim 12, wherein:
the second imaging device comprises a plurality of light emitting diodes (LEDs); and
the at least one computing device is further directed to adjust at least one of: a red value, a blue value, and a green value associated with an illumination of at least one of the plurality of LEDs.

14. The system of claim 5, wherein the at least one computing device is further directed to apply a machine learning routine to improve future detection of the identity of the pill.

15. A computer-implemented method, comprising:
selectively controlling, by at least one computing device, illumination of a pill provided at an imaging position by a pill dispensing system;
directing, by the at least one computing device, an imaging device to capture image data of the pill during illumination of the pill from a position above the pill and illumination of the pill from a position beneath the pill;
generating, by the at least one computing device, a digital fingerprint of the pill comprising histogram data, the histogram data generated based at least in part on the image data captured by the imaging device;
determining, by the at least one computing device, an identity of the pill based at least in part on a comparison of the digital fingerprint to a digital fingerprint library; and
applying, by the at least one computing device, a machine learning routine to improve future detection of the identity of the pill.

16. The computer-implemented method of claim 15, wherein the histogram data comprises data associated with a red-green-blue histogram generated based at least in part on the image data captured by the imaging device.

17. The computer-implemented method of claim 15, wherein the digital fingerprint further comprises a pill edge morphology generated based at least in part on the image data captured by the imaging device.

18. The computer-implemented method of claim 15, further comprising directing, by the at least one computing device, a first lighting device to illuminate the pill from a position underneath the pill.

19. The computer-implemented method of claim 18, further comprising directing, by the at least one computing device, a second lighting device positioned near an imaging device to illuminate the pill from a position above the pill.

20. The computer-implemented method of claim 19, wherein:
the image data comprises at least a first image and a second image;
the first image is acquired by the imaging device when the pill is illuminated by the first lighting device from the position underneath the pill;
the second image is acquired by the imaging device when the pill is illuminated by the second lighting device from the position above the pill;
the pill edge morphology is generated based at least in part on the first image; and
the red-green-blue histogram is generated based at least in part on the second image.

* * * * *